US011490972B2

(12) United States Patent
Betsugi et al.

(10) Patent No.: US 11,490,972 B2
(45) Date of Patent: Nov. 8, 2022

(54) DRIVER INTERFACE, ROBOTIC SURGICAL SYSTEM, AND METHOD OF DETECTING ATTACHMENT OF DRAPE TO DRIVER INTERFACE

(71) Applicant: MEDICAROID CORPORATION, Kobe (JP)

(72) Inventors: Shota Betsugi, Kobe (JP); Kenji Ago, Kobe (JP)

(73) Assignee: MEDICAROID CORPORATION, Kobe (JP)

(*) Notice: Subject to any disclaimer, the term of this patent is extended or adjusted under 35 U.S.C. 154(b) by 438 days.

(21) Appl. No.: 16/553,095

(22) Filed: Aug. 27, 2019

(65) Prior Publication Data

US 2020/0069383 A1 Mar. 5, 2020

(30) Foreign Application Priority Data

Aug. 28, 2018 (JP) .............................. JP2018-159333

(51) Int. Cl.
| | |
|---|---|
| *A61B 34/30* | (2016.01) |
| *A61B 34/00* | (2016.01) |
| *A61B 90/50* | (2016.01) |
| *A61B 46/10* | (2016.01) |
| *A61B 90/00* | (2016.01) |
| *A61B 17/00* | (2006.01) |

(52) U.S. Cl.
CPC .............. *A61B 34/30* (2016.02); *A61B 34/25* (2016.02); *A61B 46/10* (2016.02); *A61B 90/50* (2016.02); *A61B 34/71* (2016.02); *A61B 90/361* (2016.02); *A61B 2017/00477* (2013.01); *A61B 2017/00973* (2013.01); *A61B 2034/305* (2016.02)

(58) Field of Classification Search
CPC ....... A61B 34/30; A61B 34/25; A61B 19/201; A61B 19/203; A61B 19/5244; A61B 90/50

See application file for complete search history.

(56) References Cited

U.S. PATENT DOCUMENTS

| | | | | |
|---|---|---|---|---|
| 8,142,447 B2* | 3/2012 | Cooper | .................. | G16H 40/63 606/1 |
| 2018/0228559 A1* | 8/2018 | Brierton | ................. | A61B 90/98 |

FOREIGN PATENT DOCUMENTS

| | | |
|---|---|---|
| WO | 2018/013305 A1 | 1/2018 |
| WO | 2018/118922 A1 | 6/2018 |

* cited by examiner

*Primary Examiner* — Vi X Nguyen
(74) *Attorney, Agent, or Firm* — Metrolex IP Law Group, PLLC

(57) ABSTRACT

A driver interface provided to a robot arm of a robotic surgical system according to an embodiment may include: a drive member provided corresponding to a drive transmission member provided on an adaptor; an actuator to drive the drive member to rotate; and a housing accommodating the actuator therein and including a drive member opening at a location corresponding to the drive member and a drape detection opening. The driver interface may further include a detection member movable between a protrusion position at which a part of the detection member is protruded from the drape detection opening of the housing, and a withdrawal position at which the detection member is withdrawn into the drape detection opening of the housing. The driver interface may further include a sensor configured to detect the detection member is moved to the withdrawal position as a drape is brought into contact with the detection member.

20 Claims, 8 Drawing Sheets

DRAPE IS NOT MOUNTED/ADAPTOR IS NOT MOUNTED

DRAPE IS NOT MOUNTED/ADAPTOR IS MOUNTED

DRAPE IS MOUNTED/ADAPTOR IS MOUNTED

DRIVER INTERFACE, ROBOTIC SURGICAL SYSTEM, AND METHOD OF DETECTING ATTACHMENT OF DRAPE TO DRIVER INTERFACE

CROSS REFERENCE TO RELATED APPLICATIONS

This application claims priority to Japanese Patent Application No. 2018-159333 filed on Aug. 28, 2018, the entire contents of which are incorporated herein by reference.

BACKGROUND

The disclosure relates to a driver interface, a robotic surgical system, and a method of detecting attachment of a drape to the driver interface. Particularly, the disclosure relates to a driver interface provided for a robot arm of a robotic surgical system, the robotic surgical system including the driver interface, and a method of detecting attachment of a drape to the driver interface.

In a related art, robotic surgical systems for assisting surgery are known. Such robotic surgical systems generally include a patient-side apparatus with robot arms and a remote operation apparatus for remote control of the patient-side apparatus. To the robot arms of the patient-side apparatus, an endoscope and surgical instruments including forceps, for example, are attached. A doctor performs endoscopic surgery for the patient with robot arms of the patient-side apparatus by operating the remote control apparatus while checking patient endoscopic images. Using such a robotic surgical system minimizes the incision in the patient's skin, enabling minimally invasive surgery with the burden on the patient reduced.

Additionally, in a related art, a driver interface provided for a robot arm of such a robotic surgical system is known (e.g., see U.S. Pat. No. 8,142,447). U.S. Pat. No. 8,142,447 discloses an interface (a driver interface) provided for a robot arm of the robotic surgical system. This interface is connected to a tool (a surgical instrument) through an adaptor and is configured to transmit drive to the tool through the adaptor.

The adaptor is attached to the interface of the robot arm together with a sterile drape that covers the robot arm. The sterile drape is attached to the interface of the robot arm, and then the adaptor is mounted to the interface.

SUMMARY

When the sterile drape is attached to the robot arm and then the adaptor is mounted to the interface as disclosed in U.S. Pat. No. 8,142,447, the adaptor may be mounted while the sterile drape is not attached by mistake in some cases. This leads to a problem of requiring detection of attachment of the sterile drape to the robot arm in order to reliably confirm whether the sterile drape is attached to the robot arm.

An object of an embodiment of the disclosure is to provide a driver interface, a robotic surgical system, and a method of detecting attachment of a drape to the driver interface, which are capable of detecting attachment of the drape to the robot arm and also capable of recognizing that the adaptor is mounted while the sterile drape is not attached by mistake.

A first aspect of the disclosure may be a driver interface that is provided to a robot arm of a robotic surgical system and to which an adaptor is to be attached with a drape interposed between the driver interface and the adaptor. The driver interface according the first aspect may include: a drive member provided corresponding to a drive transmission member provided on the adaptor; an actuator configured to drive the drive member to rotate; a housing accommodating the actuator therein, including a drive member opening at a location corresponding to the drive member, and including a drape detection opening; a detection member provided movable between a protrusion position at which a part of the detection member is protruded from the drape detection opening of the housing, and a withdrawal position at which the detection member is withdrawn into the drape detection opening of the housing; and a sensor configured to detect the detection member is moved to the withdrawal position as the drape is brought into contact with the detection member.

A second aspect of the disclosure is a robotic surgical system. The robotic surgical system according to the second aspect may include: a robot arm; an adaptor that is attached to the robot arm with a drape covering the robot arm interposed between the robot arm and the adaptor; and a surgical instrument attached to the adaptor and including a shaft and an end effector provided at a distal end proton of the shaft. The robot arm may include a driver interface to which the adaptor is attached with the drape interposed therebetween and is configured to generate driving force to drive the end effector. The driver interface may include: a drive member provided corresponding to a drive transmission member provided on the adaptor; an actuator configured to drive the drive member to rotate; a housing accommodating the actuator therein, including a drive member opening at a location corresponding to the drive member, and including a drape detection opening; a detection member provided movable between a protrusion position at which a part of the detection member is protruded from the drape detection opening and a withdrawal position at which the detection member is withdrawn into the drape detection opening; and a sensor configured to detect the detection member is moved to the withdrawal position as the drape is brought into contact with the detection member.

A third aspect of the disclosure is a method of detecting attachment of a drape to a driver interface of a robot arm by using an adaptor. The method according to the third aspect may include: bringing the drape interposed between the adaptor and the driver interface into contact with a detection member of the driver interface; and moving the detection member, with which the drape is into contact, from a protrusion position at which the detection member is protruded from a drape detection opening of the driver interface to a withdrawal position at which the detection member is withdrawn into the drape detection opening; and detecting the detection member which is moved to the withdrawal position.

DETAILED DESCRIPTION

Figure 1:
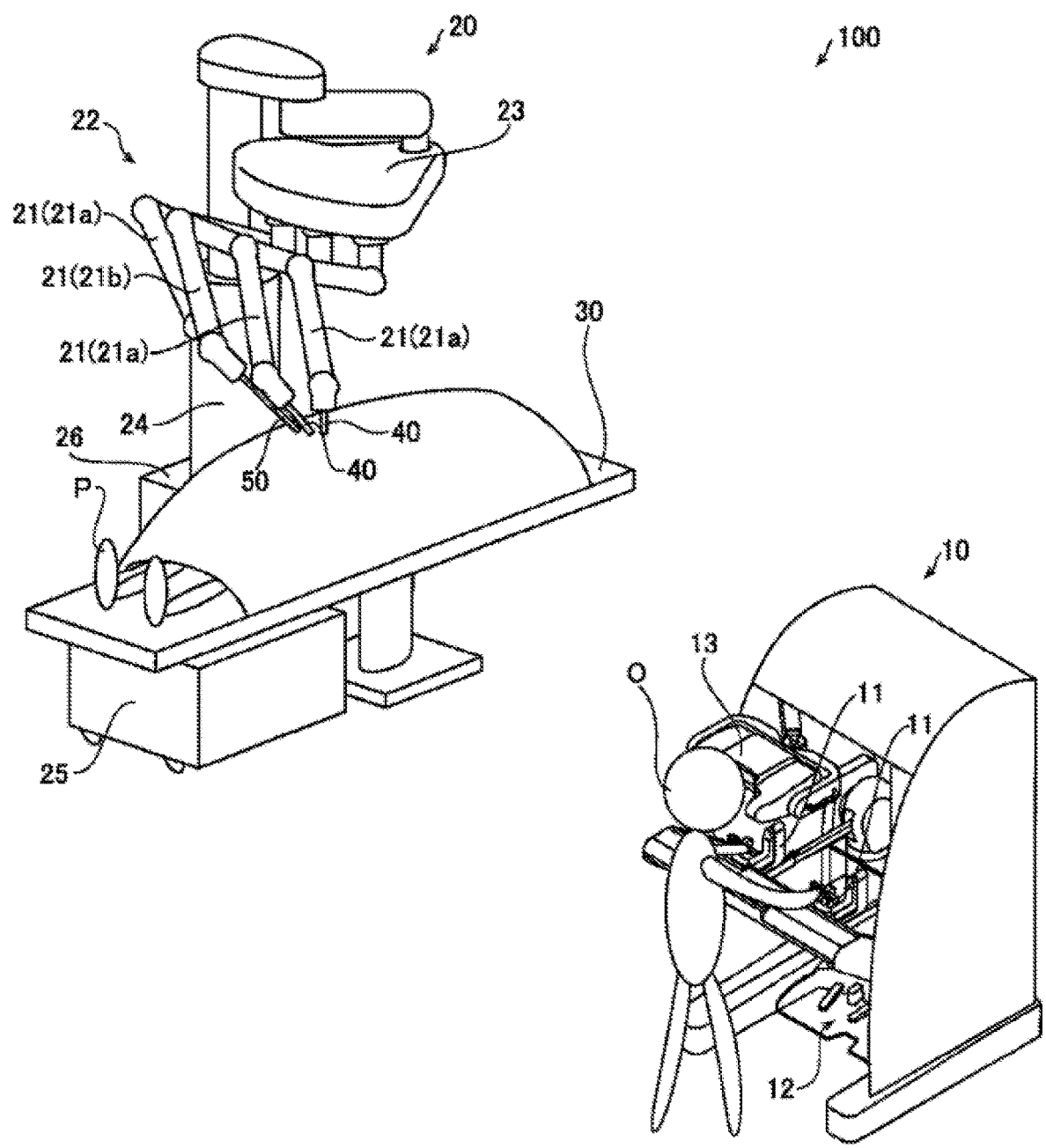
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only (Configuration of Robotic Surgical System)

The configuration of a robotic surgical system 100 according to an embodiment is described with reference to FIGS. 1 and 2.

As illustrated in FIG. 1, the robotic surgical system 100 includes a remote control apparatus 10 and a patient-side apparatus 20. The remote control apparatus 10 is provided to remotely control medical equipment provided for the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment, including surgical instruments 40 and an endoscope 50, attached to robot arms 21. This allows minimally invasive surgery.

The patient-side apparatus 20 constitutes an interface to perform a surgery on a patient P. The patient-side apparatus 20 is positioned beside an operation table 30 on which the patient P is laid. The patient-side apparatus 20 includes robot arms 21. One of the robot arms 21 (21b) holds the endoscope 50 while the other robot arms 21 (21a) hold the surgical instruments 40. The robot arms 21 are commonly supported by a platform 23. Each of the robot arms 21 includes joints. Each joint includes a driver provided with a servo-motor and a position detector such as an encoder. The robot arms 21 are configured so that the medical equipment attached to each robot arm 21 is controlled by a driving signal given through the controller 26 and performs a desired movement.

The platform 23 is supported by a positioner 22 placed on the floor of an operation room. The positioner 22 includes a column 24 and a base 25. The column 24 includes an elevating shaft adjustable in the vertical direction. The base 25 includes wheels and is movable on the floor surface.

The surgical instruments 40 as the medical equipment are detachably attached to the distal ends of the robot arms 21a. Each surgical instrument 40 includes: a housing 43 (see FIG. 4), which is attached to the robot arm 21a; an elongated shaft 42 (see FIG. 4); and an end effector 41 (see FIG. 4), which is provided at the tip or distal end portion of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image within the body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate medical equipment attached to the robot arms 21. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed, for example.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object and include an action to supply current to a bipolar or monopolar instrument to burn off the surgery site.

The action modes to be executed by the endoscope 50 include the position and posture of the tip or distal end portion of the endoscope 50 and setting of the zoom magnification, for example.

Figure 2:
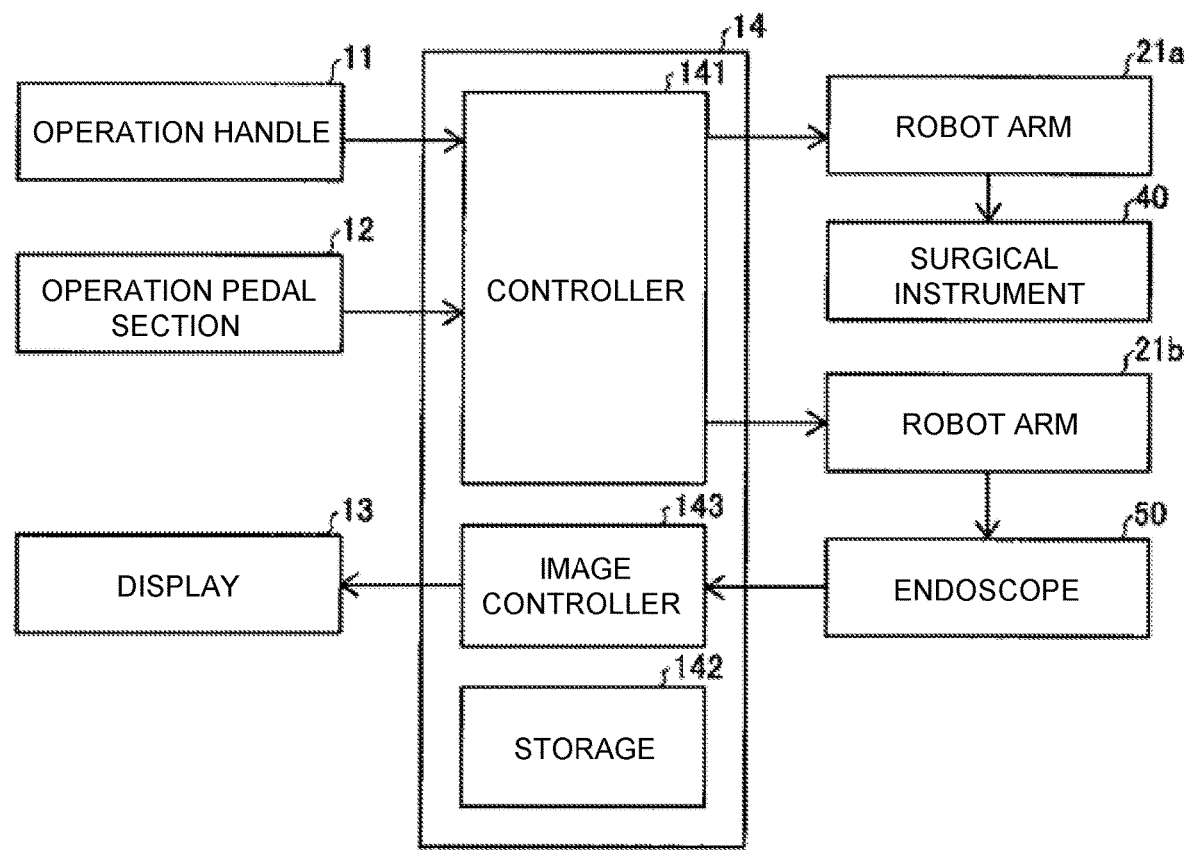
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display section 13, and a control apparatus 14.

The operation handles 11 are provided in order to remotely operate medical equipment attached to the robot arms 21. Specifically, the operation handles 11 accept operations by the operator O for operating medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section on the master side in the master-slave system, and the robot arms 21a and 21b holding medical equipment constitute an operating section on the slave side. When the operator O operates the operation handles 11, the movement of one of the robot arms 21a or 21b is controlled so that the tip (the end effector 41 of the surgical instrument 40) of the robot arm 21a or the tip (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows precise fine surgery.

The operation pedal section 12 includes pedals to execute medical equipment-related functions. The pedals include a coagulation pedal, a cutting pedal, a camera pedal, and a clutch pedal. The pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. The position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21 to stop movement of the surgical instruments 40. Specifically, when the clutch pedal is being pressed, the robot arms 21 of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21. The operator O restarts the operation for the operation handles 11 around the center thereof.

The display section 13 is configured to display images captured by the endoscope 50. The display section 13 includes a scope type display section or a non-scope type display section. The scope type display section is a display section that the operator O looks into. The non-scope type display section is a display section like an open-type display section that includes a flat screen and the operator O is able to see without looking into, such as normal displays for personal computers.

When the scope type display section is attached, the scope type display section displays 3D images captured by the endoscope 50 attached to the robot arm 21b of the patient-side apparatus 20. When the non-scope type display section is attached, the non-scope type display section also displays 3D images captured by the endoscope 50 provided for the patient-side apparatus 20. The non-scope type display section may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be formed of a single controller performing centralized control or may be composed of controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display section 13. The image controller 143 performs processing and alternations for the images when needed. (Configurations of Surgical Instrument, Adaptor, Drape, and Robot Arm)

With reference to FIGS. 3 to 10, the configurations of the surgical instrument 40, an adaptor 60, a drape 70, and the robot arm 21 according to an embodiment are described.

(Attachment Condition)

Figure 3:
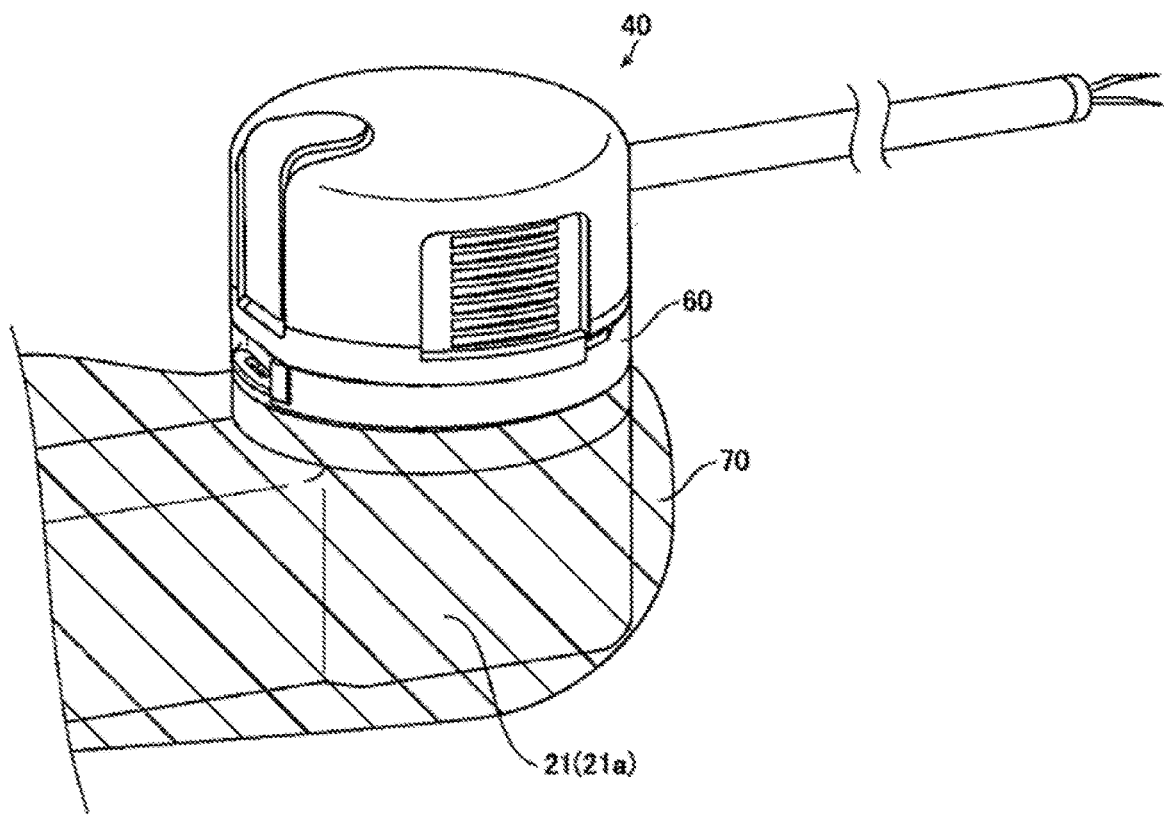
FIG. 3 is a diagram illustrating a perspective view illustrating a state where a surgical instrument is attached to a robot arm through an adaptor according to an embodiment.
Figure 4:
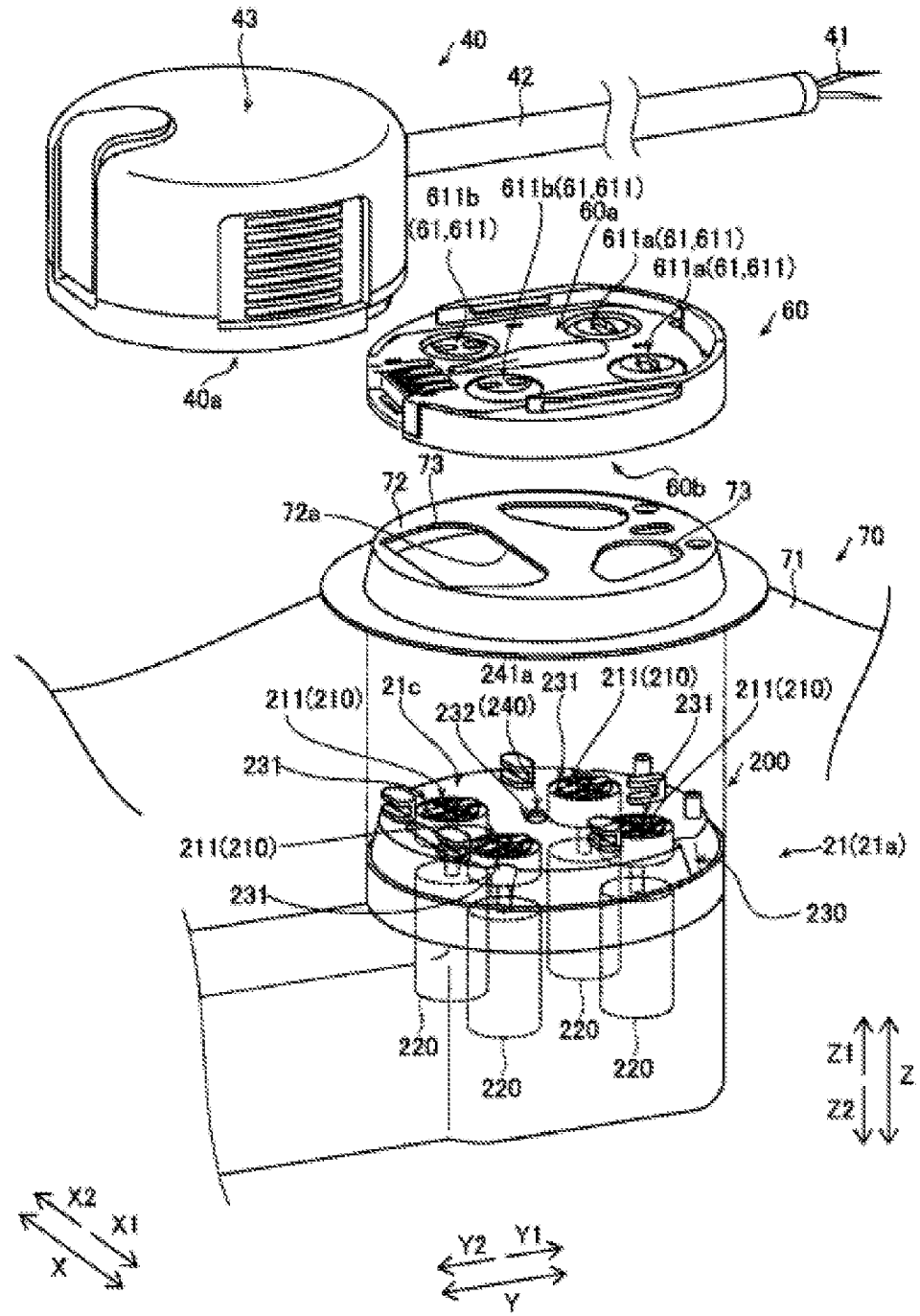
FIG. 4 is a diagram illustrating a perspective view of a state where the adaptor and the surgical instrument are detached from the robot arm according to an embodiment.
Figure 5:
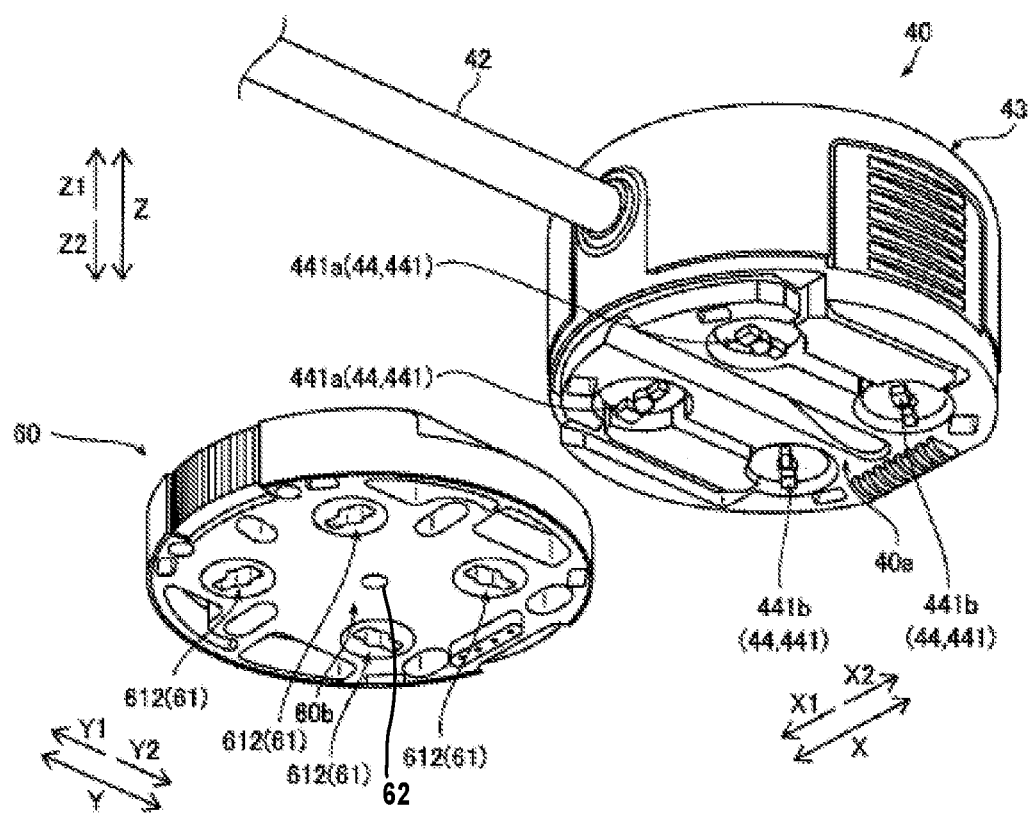
FIG. 5 is a diagram illustrating perspective views of the adaptor and surgical instrument according to an embodiment as seen from the Z2 direction.

As illustrated in FIGS. 3 to 5, the surgical instrument 40 is detachably connected to the robot arm 21 through the adaptor 60. The adaptor 60 is a drape adaptor configured to sandwich the sterile drape 70 to cover the robot arm 21, in conjunction with the robot arm 21. The adaptor 60 is attached to an attachment surface 40a of a housing 43 on the Z2 side of the surgical instrument 40. The surgical instrument 40 is attached to an attachment surface 60a of the adaptor 60 on the Z1 side. The robot arm 21 is attached to an attachment surface 60b of the adaptor 60 on the Z2 side. The adaptor 60 is attached to an attachment surface 21c of the robot arm 21 on the Z1 side.

The robot arm 21 is used in a clean area and is covered with a drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drapes 70.

The drape 70 includes a body section 71 and an attachment section 72. The body section 71 covers the robot arm 21. The attachment section 72 is sandwiched between the robot arm 21 and the adaptor 60. The body section 71 is made of a flexible film member. The flexible film member is made of a resin material, such as thermoplastic polyurethane and polyethylene. The body section 71 includes an opening so that the robot arm 21 is engaged with the adaptor 60. In the opening of the body section 71, the attachment section 72 is provided so as to close the opening. The attachment section 72 is made of a resin mold member in a film form. The resin mold member is made of a resin member such as polyethylene terephthalate. The attachment section 72 is formed to be thicker and harder (less flexible) than the body section 71. The attachment section 72 includes an opening 73 so that the robot arm 21 is engaged with the adaptor 60. The opening 73 may be provided corresponding to the section where the robot arm 21 is engaged with the adaptor 60. Openings 73 may be provided corresponding to plural sections at which the robot arm 21 is engaged with the adaptor 60.

The surgical instrument 40 includes plural (four) driven members 44 (see FIG. 5), which are provided within the housing 43 and are rotatable about the respective rotation axes extending in the Z direction. The plural driven members 44 are provided to operate (drive) the end effector 41. For example, the driven members 44 are connected to the end effector 41 with wires (not illustrated) inserted through the shaft 42. The driven members 44 are rotated to drive the wires, which operate (drive) the end effector 41. In addition, the driven members 44 are connected to the shaft 42 through gears (not illustrated), for example. The shaft 42 is thereby rotated with rotation of the driven members 44, and the end effector 41 is operated with the rotation of the shaft 42.

To transmit driving force from the robot arm 21, the driven members 44 include engagement protrusions 441, which are engaged with the later-described drive transmission members 61 of the adaptor 60. The engagement protrusions 441 protrude from the Z2-side surfaces of the respective driven members 44 toward the adaptor 60 (in the Z2 direction). The engagement protrusions 441 include engagement protrusions 441a, which are provided for the driven members 44 positioned on the Y1 side, and engagement protrusions 441b, which are provided for the driven members 44 positioned on the Y2 side. The engagement protrusions 441a are different in shape from the engagement protrusions 441b. The shapes of the engagement protrusions 441a and 441b correspond to the later-described engagement recesses 611a and 611b of the adaptor 60, respectively.

The adaptor 60 includes plural (four) drive transmission members 61, which are provided corresponding to the plural (four) driven members 44 of the surgical instrument 40. Each drive transmission member 61 is rotatable about a rotation axis, which extends in the Z direction. The drive transmission members 61 are provided to transmit driving force from the robot arm 21 to the driven members 44 of the surgical instrument 40. The drive transmission members 61 include engagement recesses 611 (see FIG. 4), which are engaged with the engagement protrusions 441 of the driven members 44 of the surgical instrument 40. Each engagement recess 611 is located in the surgical instrument 40 side (the Z1 side) of the drive transmission member 61 and is recessed from the Z1 side surface of the drive transmission member 61, in the Z2 direction, opposite to the surgical instrument 40. The engagement recesses 611 include the engagement recesses 611a, which are provided for the drive transmission members 61 positioned on the Y1 side, and the engagement recesses 611b, which are provided for the drive transmission members 61 positioned on the Y2 side. The engagement recesses 611a are different in shape from the engagement recesses 611b.

Each drive transmission member 61 includes an engagement recess 612 (see FIG. 5), which is engaged with the later-described engagement protrusion 211 of the robot arm 21. The engagement recess 612 is located in the robot arm 21 side (on the Z2 side) of the drive transmission member 61 and is recessed from the Z2 side surface of the drive transmission member 61, in the Z1 direction, opposite to the robot arm 21.

As illustrated in FIG. 4, the robot arm 21 includes a driver interface 200 to transmit drive to the surgical instrument 40 through the drive transmission members 61 of the adaptor 60. The driver interface 200 generates driving force to drive the end effector 41 of the surgical instrument 40. The drape 70 is attached to the driver interface 200 with the adaptor 60 interposed in between. The driver interface 200 includes: plural (four) drive members 210, which are provided corresponding to the plural (four) drive transmission members 61 of the adaptor 60; and plural (four) actuators 220, which are provided corresponding to the drive members 210.

The drive members 210 are rotated about rotation axes extending in the Z direction. Each drive member 210 includes the engagement protrusion 211 that is engaged with the engagement recess 612 of the drive transmission member 61 of the adaptor 60. The engagement protrusion 211 is provided to protrude from a surface on the adaptor 60-side (the Z1-side) of the drive member 210 toward the adaptor 60. Each actuator 220 includes a motor and rotates the corresponding drive member 210 about the rotation axis extending in the Z direction.

The driver interface 200 includes a housing 230 that houses the actuators 220. The housing 230 includes plural (four) drive member openings 231 at locations corresponding to the drive members 210. The drive member openings 231 are through-holes that pass through the Z1-side surface of the housing 230 in the Z direction. The drive member openings 231 expose a part of the drive members 210 arranged inside the housing 230 to the outside of the housing 230. The drive member openings 231 are formed in a substantially circular shape as seen from the Z direction. The housing 230 includes a single drape detection opening 232 at location corresponding to the later-described detection member 240. The drape detection opening 232 is a through-hole that passes through the Z1-side surface of the housing 230 in the Z direction. The drape detection opening 232 exposes a part (a later-described contact section 241a) of the detection member 240 arranged inside the housing 230 to the outside of the housing 230. The drape detection opening 232 is formed in a substantially circular shape as seen from the Z direction. The diameter of the drape detection opening 232 is smaller than the diameter of each drive member opening 231.

Figure 6:
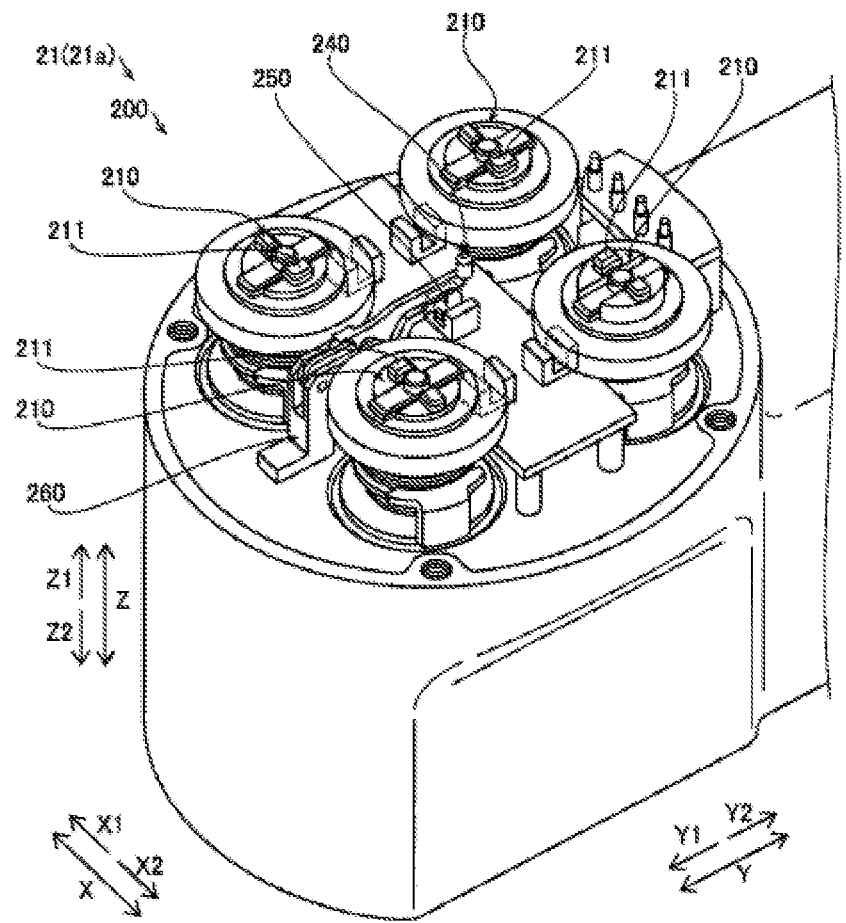
FIG. 6 is a diagram illustrating a perspective view of a state where a housing of a driver interface of the robot arm is removed according to an embodiment.

As illustrated in FIG. 6, the driver interface 200 includes the detection member 240 and a sensor 250 that are arranged inside the housing 230 and detect attachment of the drape 70 to the robot arm 21. In an embodiment, the detection member 240 is arranged so as to be movable between a protrusion position P1 (see FIGS. 10A and 10B) and a withdrawal position P2 (see FIG. 10O). The detection member 240 protrudes from the drape detection opening 232 in the protrusion position P1 and withdraws from the drape detection opening 232 in the withdrawal position P2. The sensor 250 is configured to detect the detection member 240 that is moved to the withdrawal position P2 as the drape 70 is brought into contact with the detection member 240. Since the sensor 250 detects the detection member 240 that is moved to the withdrawal position P2 as the drape 70 is brought into contact with the detection member 240, it is possible to detect attachment of the drape 70 to the robot arm 21. Additionally, since the detection member 240 is not moved to the withdrawal position P2 when the adaptor 60 is mounted without attaching the drape 70 to the robot arm 21, it is also possible to recognize that the adaptor 60 is mounted while the drape 70 is not attached by mistake. Consequently, it is possible to detect attachment of the drape 70 to the robot arm 21 and also to recognize that the adaptor 60 is mounted while the drape 70 is not attached by mistake.

Figure 7:
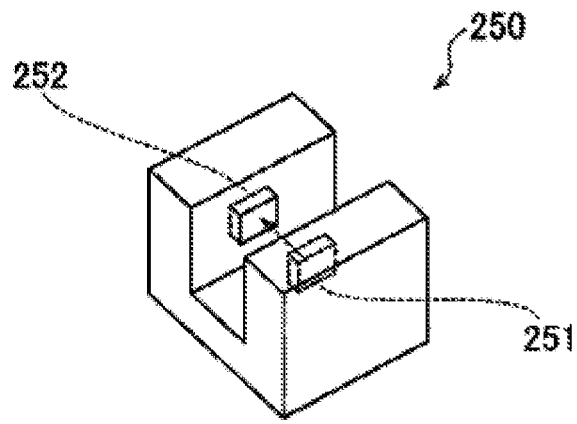
FIG. 7 is a diagram illustrating a perspective view of a sensor according to an embodiment.

As illustrated in FIG. 7, the sensor 250 is an optical sensor. The detection member 240 is easily detected by using a change in amount of received light due to movement of the detection member 240. Specifically, the sensor 250 is a light-transmissive optical photomicro sensor including an emitter 251 that emits light and a receiver 252 that receives the light from the emitter 251. The sensor 250 is configured to detect the detection member 240 set in the protrusion position P1 upon light blockage due to the later-described detection section 242a of the detection member 240 (see FIG. 10A). Additionally, the sensor 250 is configured to detect the detection member 240 moved to the withdrawal position P2 upon no light blockage due to the detection section 242a of the detection member 240 (see FIG. 10O). When the sensor 250 does not emit light because of failure, it is possible to recognize that the drape 70 is not attached, like during the light blockage due to the detection member 240. Consequently, even during the failure of the sensor 250, it is possible to prevent wrong recognition that the drape 70 is attached.

Figure 8:
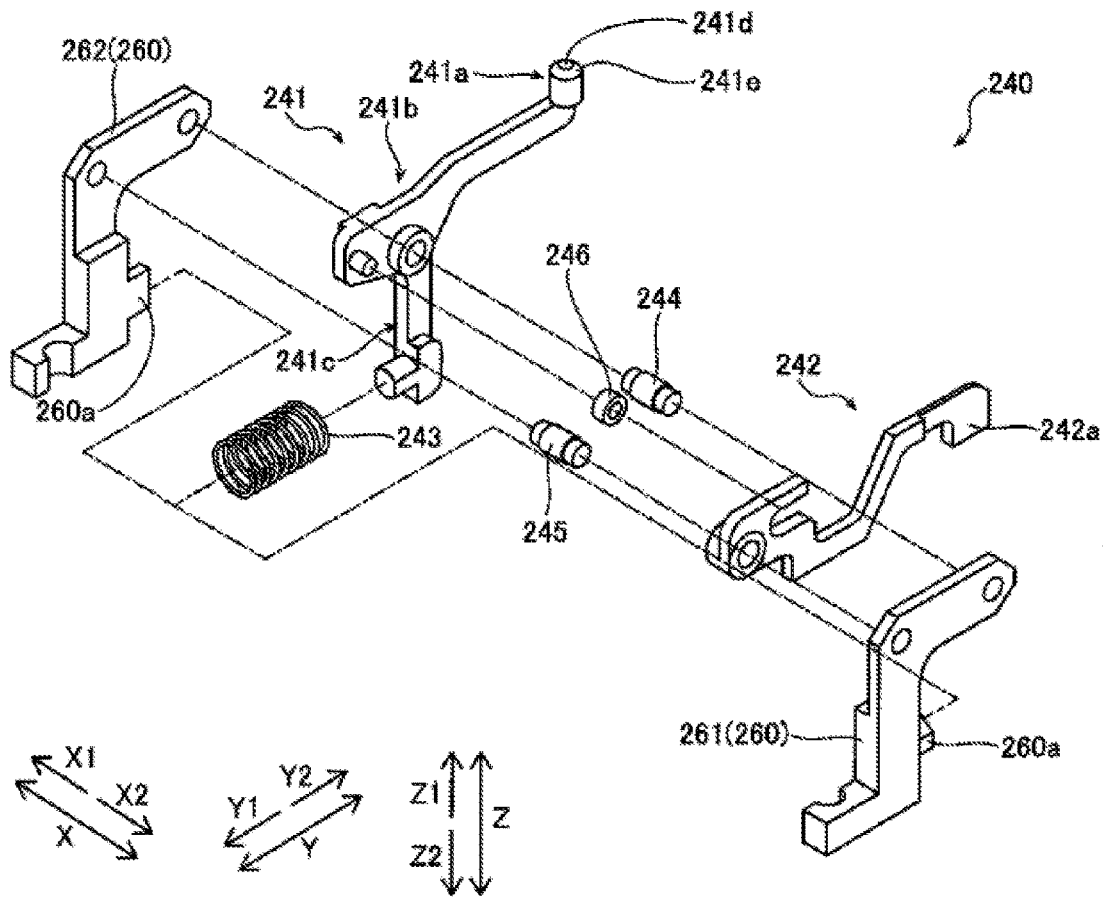
FIG. 8 is a diagram illustrating an exploded perspective view of a detection member according to an embodiment.
Figure 9:
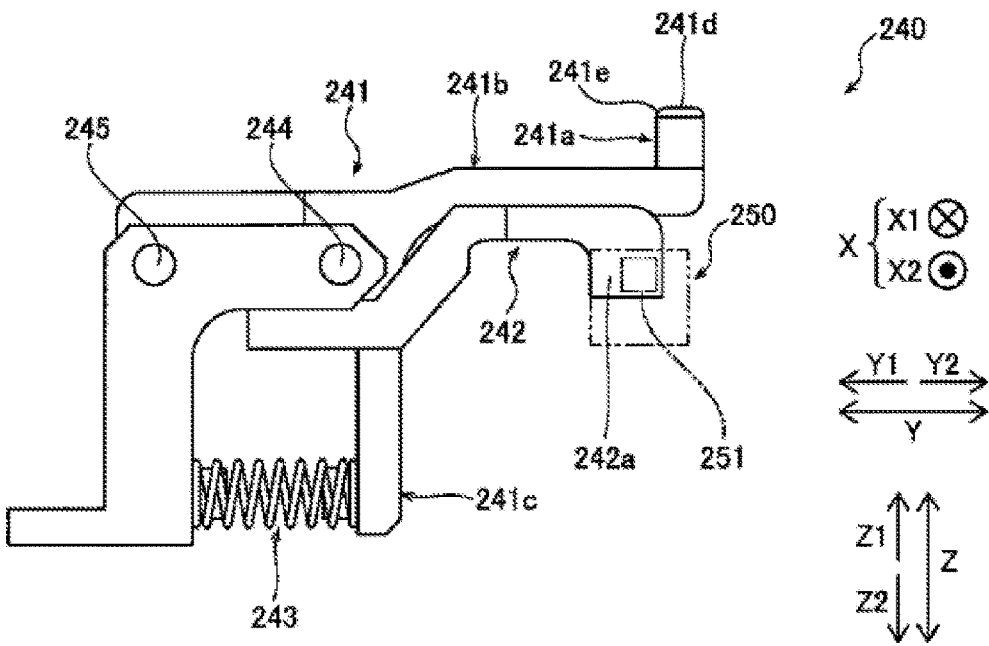
FIG. 9 is a diagram illustrating a view of the detection member according to an embodiment as seen from the X2 direction.

As illustrated in FIGS. 8 and 9, the detection member 240 includes an arm member 241, an arm member 242, and a spring 243. The arm member 241 is an example of a first arm member, and the arm member 242 is an example of a second arm member. The detection member 240 is provided to be rotatably supported by support members 260. The support members 260 include a pair of support members 261 and 262 opposed to each other in the X direction. The pair of support members 261 and 262 are provided to support the detection member 240 so as to sandwich the detection member 240 in the X direction. The pair of support members 261 and 262 are fixed to the robot arm 21 by, for example, screws.

The arm member 241 is configured to be rotatable about a rotation axis extending in the X direction. Specifically, the arm member 241 is supported by the support members 260 rotatably about the rotation axis extending in the X direction through a pivot shaft part 244. The arm member 241 includes the contact section 241a that includes a part protruding from the drape detection opening 232 and that comes into contact with an attachment surface 72a on the robot arm 21-side (the Z2 side) of the attachment section 72 of the drape 70. The arm member 241 is configured to be rotated about the rotation axis extending in the X direction and move the contact section 241a between the protrusion position P1 and the withdrawal position P2. This makes it possible to move the contact section 241a of the detection member 240 even with small force. Consequently, even when the drape 70 that is made of relatively soft material is brought into contact with the detection member 240 to move the detection member 240, it is possible to reduce the loads on the drape 70.

The arm member 241 includes an arm section 241b and a spring attachment section 241c. The arm section 241b extends in the Y direction substantially orthogonal to the X direction. The spring attachment section 241c is provided to protrude toward the Z2 side from the arm section 241b. The arm section 241b of the arm member 241 includes the contact section 241a near one end in the Y direction. Additionally, the arm section 241b of the arm member 241 includes the pivot shaft part 244 near the other end in the Y direction. The arm length (a length from the contact section 241a to the pivot shaft part 244) of the arm section 241b of the arm member 241 can be made long. Consequently, it is possible to move the contact section 241a of the detection member 240 with smaller force.

The contact section 241a is provided to protrude toward the Z1 side from near the one end of the arm section 241 b of the arm member 241. The contact section 241a includes a flat surface section 241d arranged on the Z1 side. The flat surface section 241d is provided to come into contact with the attachment surface 72a of the attachment section 72 of the drape 70. Since surface contact between the drape 70 and the flat surface section 241d of the contact section 241a can be made, it is possible to reduce the loads on the drape 70 when the drape 70 is brought into contact with the contact section 241a. A rim 241e or an edge 241e of the flat surface section 241d of the contact section 241a is formed to be chamfered in an arc or a rounded shape (a curved surface shape). This makes it possible to reduce the loads on the drape 70 more than a case where the rim 241e of the flat surface section 241d of the contact section 241a is formed in a rectangular shape or pointed. The contact section 241a is formed in a substantially circular shape as seen from the Z direction.

One end of the spring 243 is attached to the spring attachment section 241c. The other end of the spring 243 is attached to spring attachment sections 260a of the support members 260. The spring attachment sections 260a are respectively formed on the pair of support members 261 and 262. The spring attachment section 241c is provided to hold the spring 243 between the support members 260. The spring 243 is provided to bias the detection member 240 to set the detection member 240 in the protrusion position P1. This makes it possible to reliably set the detection member 240 in the protrusion position P1 when the drape 70 is not attached. Specifically, the spring 243 is provided to bias the detection member 240 toward the Y2 side. The spring 243 is a compression spring (a compression coil spring). The detection member 240 is configured to be moved from the protrusion position P1 to the withdrawal position P2 against the bias force of the spring 243. The detection member 240 is configured to be moved from the withdrawal position P2 to the protrusion position P1 by the bias force of the spring 243. The detection member 240 is provided to be movable between the protrusion position P1 and the withdrawal position P2 using the spring 243.

The arm member 242 is configured to be rotatable about the rotation axis extending in the X direction. Specifically, the arm member 242 is supported by the support members 260 rotatably about the rotation axis extending in the X direction through a pivot shaft part 245. The pivot shaft part 244 of the arm member 241 and the pivot shaft part 245 of the arm member 242 are provided in different positions in the Y direction. In other words, the pivot shaft part of the arm member 241 and the pivot shaft part of the arm member 242 are arranged to be deviated from each other in the Y direction. The arm member 242 is provided to extend in the Y direction. The arm member 242 includes a detection section 242a near one end in the Y direction. The detection section 242a is provided to block the light toward the sensor 250. The detection section 242a is configured to block the light toward the sensor 250 when the detection member 240 is set in the protrusion position P1. The detection section 242a is configured not to block the light toward the sensor 250 when the detection member 240 is set in the withdrawal position P2. The detection section 242a is formed in a flat plate shape. The arm member 242 includes the pivot shaft part 245 near the other end in the Y direction.

The arm member 242 is connected to the arm member 241 in a manner movable together with the arm member 241 with a connection member 246 interposed in between. The arm member 242 and the arm member 241 are connected to each other with the connection member 246 interposed in between such that the arm member 242 and the arm member 241 are rotated in the opposite directions. Specifically, when the arm member 241 is rotated such that the contact section 241a of the arm member 241 is moved from the protrusion position P1 to the withdrawal position P2, the arm member 242 is rotated by the connection member 246 such that the detection section 242a of the arm member 242 is moved from the position at which the detection section 242a blocks the light toward the sensor 250 to the position at which the detection section 242a does not block the light toward the sensor 250. On the other hand, when the arm member 241 is rotated such that the contact section 241a of the arm member 241 is moved from the withdrawal position P2 to the protrusion position P1, the arm member 242 is rotated by the connection member 246 such that the detection section 242a of the arm member 242 is moved from the position at which the detection section 242a does not block the light toward the sensor 250 to the position at which the detection section 242a blocks the light toward the sensor 250. The connection member 246 is a bearing.

Figure 10A:
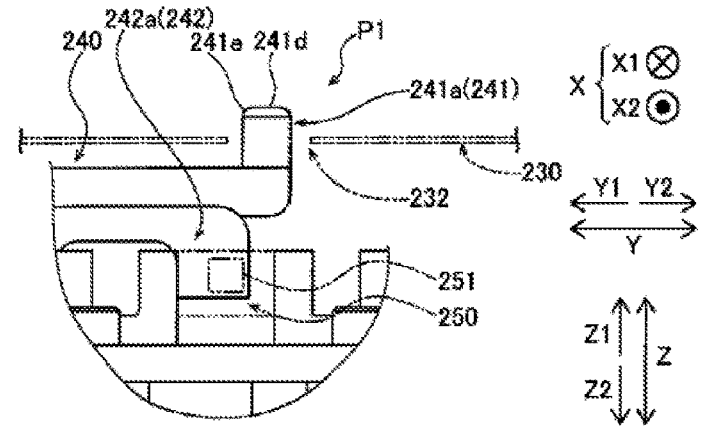
FIG. 10A is a diagram illustrating a view of a state of the detection member according to an embodiment to which neither the drape nor the adaptor is mounted.

As illustrated in FIG. 10A, in the case where the drape 70 is not attached to the robot arm 21 and the adaptor 60 is not mounted, the detection member 240 is configured to be set in the protrusion position P1. In this state, the contact section 241a of the arm member 241 of the detection member 240 is set in the protrusion position P1, and the detection section 242a of the arm member 242 is set in the position at which the detection section 242a blocks the light toward the sensor 250.

The adaptor 60 is provided with a recess 62 (see FIG. 5) that is provided at a location corresponding to the drape detection opening 232 and the contact section 241a. The recess 62 is a through-hole that passes through the attachment surface 60b of the adaptor 60 in the Z direction. Instead of the through-hole, the recess 62 may be a dent that is recessed from the attachment surface 60b toward the Z1 side. The recess 62 is formed large enough to house the contact section 241a. The attachment section 72 of the drape 70 is provided to cover (close) the recess 62 of the adaptor 60 with the drape 70 attached to the robot arm 21.

Figure 10B:
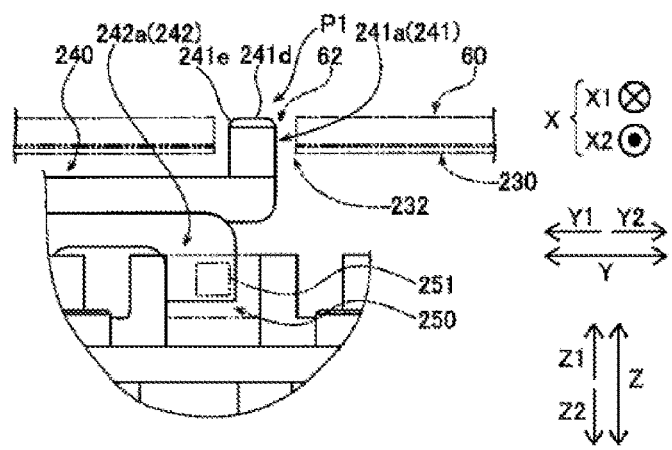
FIG. 10B is a diagram illustrating a view of a state of the detection member according to an embodiment to which the adaptor is mounted with no drape.
Figure 10C:
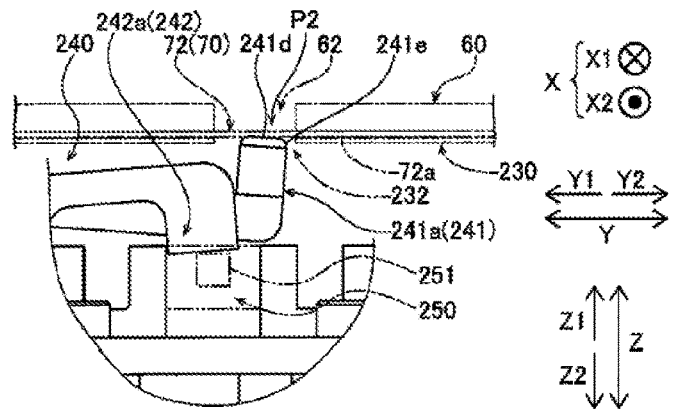
FIG. 10C is a diagram illustrating a view of a state of the detection member according to an embodiment to which the adaptor is mounted with the drape.

In an embodiment, as illustrated in FIG. 10B, in the case where the adaptor 60 is mounted without attaching the drape 70 to the robot arm 21, the detection member 240 is configured not to be moved from the protrusion position P1, with the contact section 241a inserted in the recess 62. Since the detection member 240 is not moved to the protrusion position P2 when the adaptor 60 is mounted without attaching the drape 70 to the robot arm 21, it is also possible to recognize that the adaptor 60 is mounted while the drape 70 is not attached by mistake. In this state, since the detection member 240 is kept from leaving the protrusion position P1, the contact section 241a of the arm member 241 of the detection member 240 is set in the protrusion position P1, and the detection section 242a of the arm member 242 is set in the position at which the detection section 242a blocks the light toward the sensor 250 like the case illustrated in FIG. 10A.

As illustrated in FIG. 10O, in the case where the adaptor 60 is mounted with the drape 70 attached to the robot arm 21, the detection member 240 is configured to be moved to the withdrawal position P2 as the attachment section 72 of the drape 70 covering the recess 62 of the adaptor 60 is brought into contact with the detection member 240. When the drape 70 and the adaptor 60 are correctly attached, it is possible to detect the attachment of the drape 70 to the robot arm 21. In this state, since the detection member 240 is moved to the withdrawal position P2, the contact section 241a of the arm member 241 is set in the withdrawal position P2, and, by the rotation of the arm member 242, the detection section 242a of the arm member 242 is set in the position at which the detection section 242a does not block the light toward the sensor 250.

MODIFICATIONS

It should be understood that the above-described one or more embodiments are illustrated by way of example in every respect and does not limit the invention. The scope of the invention is indicated by claims, not by explanation of the embodiments, and includes equivalents to claims and all alterations (modifications) within the same.

For example, the sensor is an optical sensor in the example illustrated in the above-described one or more embodiments, but the invention is not limited thereto. The sensor may be other than an optical sensor in an embodiment or a modification. For example, the sensor may be a switch such as a microswitch.

The sensor is configured to detect the detection member in the protrusion position when the detection member blocks the light toward the sensor and configured to detect the detection member moved to the withdrawal position when the detection member does not block the light toward the sensor in the example illustrated in the above-described one or embodiments, but the invention is not limited thereto. The sensor may be configured to detect the detection member moved to the withdrawal position when the detection member blocks the light toward the sensor and may be configured to detect the detection member in the protrusion position when the detection member does not block the light toward the sensor in an embodiment or a modification. It is possible to simplify the configuration of the detection member with such a configuration.

The detection member includes the two arm members in the example illustrated in an above-described embodiment, but the invention is not limited thereto. The detection member may include only one arm member in an embodiment or a modification. Or, the detection member may not necessarily include the arm member.

The arm member includes the contact section near one end and includes the pivot shaft part near the other end in the example illustrated in an above-described one or more embodiments, but the invention is not limited thereto. The arm member may not necessarily include the contact section near one end and may not necessarily include the pivot shaft part near the other end in an embodiment or a modification.

The contact section of the arm member includes the flat surface section that comes into contact with the drape in the example illustrated in the above-described one or more embodiments, but the invention is not limited thereto. The contact section of the arm member may not necessarily include the flat surface section that comes into contact with the drape in an embodiment or a modification. For example, the contact section of the arm member may include a curved surface section that comes into contact with the drape.

The rim of the flat surface section of the contact section of the arm member is formed in a circular shape (a curved surface shape) in the example illustrated in the above-described one or more embodiments, but the invention is not limited thereto. The rim of the flat surface section of the contact section of the arm member may not be formed in a circular shape in an embodiment or a modification. For example, the rim of the flat surface section of the contact section of the arm member may be formed in an inclined surface shape.

Each number of the provided drive transmission members, drive members, and actuators is four in the example illustrated in the above-described one or more embodiments, but the invention is not limited thereto. Each number of the provided drive transmission members, drive members, and actuators may be a plural number other than four in an embodiment or a modification.

The invention claimed is:

1. A driver interface that is provided to a robot arm of a robotic surgical system and to which an adaptor is to be attached with a drape interposed between the driver interface and the adaptor, comprising:
    a drive member provided corresponding to a drive transmission member provided on the adaptor;
    an actuator configured to drive the drive member to rotate;
    a housing accommodating the actuator therein, including a drive member opening at a location corresponding to the drive member, and including a drape detection opening;
    a detection member provided movable between a protrusion position at which a part of the detection member is protruded from the drape detection opening of the housing to an outside of the housing, and a withdrawal position at which the detection member is withdrawn toward an inside of the housing through the drape detection opening; and
    a sensor configured to detect that the detection member is moved to the withdrawal position as the drape is brought into contact with the detection member.

2. The driver interface according to claim 1, wherein the sensor is an optical sensor.

3. The driver interface according to claim 2, wherein the sensor is a light-transmissive optical sensor,
    the sensor detects the detection member at the protrusion position when the detection member blocks light toward the sensor, and
    the sensor detects the detection member at the withdrawal position when the detection member does not block the light toward the sensor.

4. The driver interface according to claim 1, wherein the detection member includes a contact section, wherein
    in the state where the detection member is at the protrusion position, the contact section of the detection member is protruded from the drape detection opening and comes into contact with the drape, and
    when the adaptor is mounted to the driver interface of the robot arm without the drape therebetween, the detection member is kept in the protrusion position, with the contact section of the detection member inserted in a recess of the adaptor provided at a location corresponding to the contact section.

5. The driver interface according to claim 4, wherein the drape is provided to cover the recess of the adaptor, and
    when the adaptor is mounted to the driver interface with the drape interposed therebetween, the detection member is moved to the withdrawal position as the drape covering the recess of the adaptor is brought into contact with the detection member.

6. The driver interface according to claim 1, wherein the detection member includes a first arm member,
    the first arm member includes a contact section of the detection member, wherein in the state where the detection member is at the protrusion position, the contact section of the detection member is protruded from the drape detection opening and comes into contact with the drape, and
    the first arm member is configured to move the contact section between the protrusion position and the withdrawal position.

7. The driver interface according to claim 6, wherein the first arm member includes the contact section in the vicinity of one end of the first arm member and includes a pivot shaft part in the vicinity of the other end of the first arm member.

8. The driver interface according to claim 6, wherein the detection member includes a second arm member that is connected to the first arm member in a manner movable together with the first arm member, and
    the second arm member includes a detection section that is detected by the sensor.

9. The driver interface according to claim 6, wherein the contact section of the first arm member includes a flat surface section that comes into contact with the drape.

10. The driver interface according to claim 9, wherein a rim of the flat surface section of the contact section is formed in a rounded shape.

11. The driver interface according to claim 1, further comprising:
a spring that biases the detection member to set the detection member in the protrusion position.

12. A driver interface that is provided to a robot arm of a robotic surgical system and to which an adaptor is to be attached with a drape interposed between the driver interface and the adaptor, comprising:
a drive member provided corresponding to a drive transmission member provided on the adaptor;
an actuator configured to drive the drive member to rotate;
a housing accommodating the actuator therein, including a drive member opening at a location corresponding to the drive member, and including a drape detection opening;
a detection member provided movable between a protrusion position at which a part of the detection member is protruded from the drape detection opening of the housing, and a withdrawal position at which the detection member is withdrawn into the drape detection opening of the housing; and
a sensor configured to detect that the detection member is moved to the withdrawal position as the drape is brought into contact with the detection member, wherein
the detection member includes a first arm member,
the first arm member includes a contact section, wherein in the state where the detection member is at the protrusion position, the contact section is protruded from the drape detection opening and comes into contact with the drape, and
the first arm member is configured to move the contact section between the protrusion position and the withdrawal position.
the first arm member includes the contact section in the vicinity of one end of the first arm member and includes a pivot shaft part in the vicinity of the other end of the first arm member,
the detection member includes a second arm member that is connected to the first arm member in a manner moveable together with the first arm member, and
the second arm member includes a detection section that is detected by the sensor.

13. The driver interface according to claim 12, wherein the second arm member includes the detection section in the vicinity of one end of the second arm member and includes a pivot shaft part in the vicinity of the other end of the second arm member.

14. The driver interface according to claim 13, wherein the pivot shaft part of the second arm member is provided in a different position from the pivot shaft part of the first arm member in a direction in which the second arm member extends.

15. The driver interface according to claim 13, wherein the first arm member and the second arm member are connected to each other with a connection member interposed in between such that the first arm member and the second arm member are rotated in opposite directions.

16. The driver interface according to claim 15, wherein the connection member is a bearing.

17. The driver interface according to claim 15, wherein the sensor is a light-transmissive optical sensor, and the detection member is configured in such a manner that:
when the first arm member is rotated such that the contact section of the first arm member is moved from the protrusion position to the withdrawal position, the second arm member is rotated such that the detection section of the second arm member is moved from a position at which the detection section blocks light toward the sensor to a position at which the detection section does not block the light toward the sensor; and
when the first arm member is rotated such that the contact section of the first arm member is moved from the withdrawal position to the protrusion position, the second arm member is rotated such that the detection section of the second arm member is moved from the position at which the detection section does not block the light toward the sensor to the position at which the detection section blocks the light toward the sensor.

18. A robotic surgical system, comprising:
a robot arm;
an adaptor that is attached to the robot arm with a drape covering the robot arm interposed between the robot arm and the adaptor; and
a surgical instrument attached to the adaptor and including a shaft and an end effector provided at a distal end proton of the shaft, wherein
the robot arm comprises a driver interface to which the adaptor is attached with the drape interposed therebetween and which is configured to generate driving force to drive the end effector, and
the driver interface includes:
a drive member provided corresponding to a drive transmission member provided on the adaptor;
an actuator configured to drive the drive member to rotate;
a housing accommodating the actuator therein, including a drive member opening at a location corresponding to the drive member, and including a drape detection opening;
a detection member provided movable between a protrusion position at which a part of the detection member is protruded from the drape detection opening to an outside of the housing and a withdrawal position at which the detection member is withdrawn toward an inside of the housing through the drape detection opening; and
a sensor configured to detect that the detection member is moved to the withdrawal position as the drape is brought into contact with the detection member.

19. The robotic surgical system according to claim 18, wherein
the detection member includes a contact section, wherein in the state where the detection member is at the protrusion position, the contact section of the detection member is protruded from the drape detection opening and comes into contact with the drape, and
the adaptor includes a recess that is provided at a location corresponding to the drape detection opening and is large enough to accommodate the contact section of the detection member therein.

20. A method of detecting attachment of a drape to a driver interface of a robot arm of a robotic surgical system by using an adaptor, wherein the driver interface includes: a drive member provided to a drive transmission member provided on the adaptor; an actuator configured to drive the drive member to rotate; a housing accommodating the actuator therein and including a drive member opening at a location corresponding to the drive member and a drape detection opening; a detection member; and a sensor, the method comprising:

bringing the drape interposed between the adaptor and the driver interface into contact with the detection member of the driver interface; and moving the detection member, with which the drape is into contact, from a protrusion position at which the detection member is protruded from the drape detection opening of the driver interface to an outside of the housing to a withdrawal position at which the detection member is withdrawn toward an inside of the housing through the drape detection opening; and detecting, by the sensor, the detection member is moved to the withdrawal position as the drape is brought into contact with the detection member.

* * * * *